US008871196B2

(12) United States Patent
Su et al.

(10) Patent No.: US 8,871,196 B2
(45) Date of Patent: Oct. 28, 2014

(54) METHOD FOR ENHANCING PPARγ EXPRESSION

(71) Applicant: Promd Biotech Co., Ltd., Tainan (TW)

(72) Inventors: Wei-Chih Su, Tainan (TW); Hsiang Ling Chen, Tainan (TW); Chun-Hsien Huang, Tainan (TW); Hsiao-Li Wu, Tainan (TW); Pei-Yu Tsai, Tainan (TW)

(73) Assignee: ProMD Biotech Co., Ltd., Tainan (TW)

( * ) Notice: Subject to any disclaimer, the term of this patent is extended or adjusted under 35 U.S.C. 154(b) by 0 days.

(21) Appl. No.: 13/922,499

(22) Filed: Jun. 20, 2013

(65) Prior Publication Data

US 2013/0344043 A1    Dec. 26, 2013

(30) Foreign Application Priority Data

Jun. 20, 2012   (TW) .............................. 101122060 A

(51) Int. Cl.
*C12N 1/20*        (2006.01)
(52) U.S. Cl.
USPC ..................... 424/93.45; 435/252.9

(58) Field of Classification Search
USPC ..................... 424/93.45; 435/252.9
See application file for complete search history.

(56) References Cited

FOREIGN PATENT DOCUMENTS

| JP | 2007284360 A | * | 11/2007 | ............. A61K 35/74 |
| KR | 2012034444 A | * | 4/2012 | ............... C12N 1/21 |

OTHER PUBLICATIONS

English machine translation of JP 2007-284360 A.*
English Abstract of KR 2012-034444 A.*

* cited by examiner

*Primary Examiner* — Rosanne Kosson
(74) *Attorney, Agent, or Firm* — Rosenberg, Klein & Lee

(57) ABSTRACT

The present invention provides a method for enhancing PPARγ expression, comprising administering a subject in need thereof an effective amount of *Lactobacillus gasseri* PM-A0005, which was deposited under Budapest Treaty in the China Center for Type Culture Collection (CCTCC), China with Deposition No. M 207039.

13 Claims, 6 Drawing Sheets (a)

(b)

METHOD FOR ENHANCING PPARγ EXPRESSION

FIELD OF THE INVENTION

The present invention relates to a method for enhancing PPARγ expression. In particular, the method comprises administering a subject in need thereof an effective amount of a specific strain.

BACKGROUND OF THE INVENTION

Peroxisome proliferator-activated receptor (PPAR) is a member of the nuclear receptors (NR) superfamily, as well as a transcription factor regulated by hormones. Different from other hormone-activated receptors, PPAR is located in the cytoplasm and then transferred into nucleus after being bound by an activated ligand; and subsequently, the complex binds to DNA response elements to activate their downstream gene expression (Glass et al., Genes Dev (2000) 14, 121-141). PPAR is a typical receptor, activated by metabolites, and is located in the nucleus. There are three types of PPARs that have been identified as α, β/δ and γ, each of which binds to a retinoid-X-receptor (RXR) to form a heterodimer receptor. The main function of PPAR β/δ is to regulate the proliferation and differentiation of gut cells. PPARγ is expressed in adipocytes, skeletal muscle cells, osteoclasts, osteoblasts and some immune cells, and its function is similar to PPARα. It was reported that it is lethal, to the subject, to knock out the PPARγ gene. The human species only has four genotypes of PPARγ, but only expresses PPARG-1 and PPARG-2 proteins in normal cells. PPARG-1 proteins are expressed extensively in cells, while PPARG-2 proteins are mainly limited to adipocytes.

It was also reported that PPARγ, activated by ligands, increased ligand-unrelated transcription activity through phosphorylation (Diradourian et al., Biochimie (2005) 87, 33-38). It was demonstrated that not only did PPARγ function as a transcription factor, PPARγ also inhibited inflammation-related gene expression by sumoylation through ligand activation. It is concluded that the function of inflammation related genes expression inhibition depends on binding the sumoylated PPARγ protein and the DNA repressor complex with the inflammation related genes, thereby preventing the 19S proteasome from degrading the repressor (Pascual et al., Nature (2005)437, 759-763).

It was reported in animal and human trials that a PPARγ activator was effective in treating diabetes and also provided anti-inflammation uses. PPARγ agonist Rosiglitazone, a type of glucocorticoid, was found to be effective in treating asthma in murine model or human trial (Narala et al., Respir Res (2007) 8, 90). Dominant negative mutation of human PPARγ results in a stereotyped syndrome of partial lipodystrophy and insulin resistance (Semple et al., J. Clin. Invest. (2006) 116, 581-589). PPARγ agonist was also often used for treating type II diabetes, e.g. pioglitazone and Rosiglitazone. It was also found that PPARγ agonist was effective in reducing bone loss and inflammation in the rheumatoid arthritis rat model (Koufany et al., Arthritis Res Ther (2008) 10, R6; Doshi et al., Expert Opin. Investig. Drugs (2010) 19(4), 489-512). In clinical trials, Rosiglitazone was also found to be effective in treating lipodystrophy (Anghel et al., Cell Res (2007) 17, 486-511).

Therefore, a new approach for enhancing PPARγ expression is desirable.

BRIEF SUMMARY OF THE INVENTION

It has been unexpectedly discovered that a specific strain, Lactobacillus gasseri PM-A0005, which was deposited under Budapest Treaty in the China Center for Type Culture Collection (CCTCC), China with Deposit No. M 207039, enhances PPARγ expression.

Therefore, in one aspect, the present invention provides a method for enhancing PPARγ expression. The method of the present invention comprises administering a subject in need thereof an effective amount of Lactobacillus gasseri (L. gasseri) PM-A0005.

The details of one or more embodiments of the present invention are set forth in the description below. Other features or advantages of the present invention will be apparent from the following detailed description of several embodiments and from the appended claims.

BRIEF DESCRIPTION OF THE DRAWINGS

The present invention is further illustrated by reference to the accompanying drawings, in which.

DETAILED DESCRIPTION OF THE INVENTION

Figure 1:
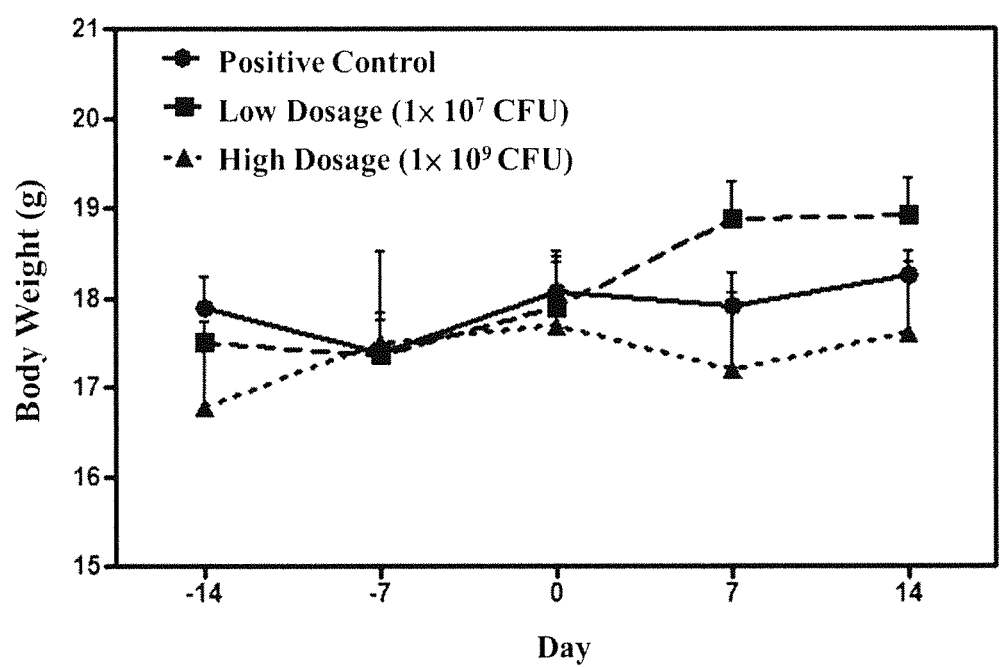
FIG. 1 shows the body weight variation of mice administered with different dosages of Lactobacillus gasseri (L. gasseri) PM-A0005 (each group n=5).

Unless defined otherwise, all technical and scientific terms used herein have the meaning commonly understood by a person skilled in the art in the field of this invention. As used herein, the following terms have the meanings ascribed to them unless specified otherwise.

As used herein, the singular forms "a", "an", and "the" include plural referents unless the context clearly indicates otherwise. For example, "an element" means one element or more elements.

According to the invention, a method for enhancing PPARγ expression is provided, which comprises administrating a subject in need thereof an effective amount of Lactobacillus gasseri (L. gasseri) PM-A0005.

The Lactobacillus gasseri PM-A0005 was deposited under Budapest Treaty in the China Center for Type Culture Collection (CCTCC), China with Deposit No. M 207039, and was first disclosed to be effective in anti-allergy in U.S. Pat. No. 8,021,868 B2 (filed on Nov. 8, 2007).

As used herein, the term "subject" refers to an animal or a human being.

As used herein, the term "effective amount" refers to an amount effective in enhancing the PPARγ expression of a subject by administered either *L. gasseri* PM-A0005 alone or in combination with another material resulting in the same activity. As commonly known in the art, the effective amount may vary according to the particular active ingredient used, the mode of administration, and the age, size, and condition of the subject to be treated.

In one embodiment of the present invention, the effective amount of *L. gasseri* PM-A0005 administered to a subject is preferably between $1 \times 10^8$ CFU/kg/day to $1 \times 10^9$ CFU/kg/day of the body weight of the subject, preferably between $5 \times 10^8$ CFU/kg/day to $6 \times 10^8$ CFU/kg/day of the body weight of the subject.

In one preferred embodiment of the present invention, the effective amount is about $5.5 \times 10^8$ CFU/kg/day of the body weight of the subject.

According to one preferred embodiment of the present invention, the composition may be orally administered to a subject at an effective amount to enhance PPARγ expression in the subject.

According to the present invention, the *L. gasseri* PM-A0005 may be prepared in a composition. In one example of the invention, the composition is a pharmaceutical composition.

The composition or pharmaceutical composition according to the invention can be prepared in any suitable form. For example, two suitable forms are a solid form suitable for oral administration, e.g. pills, capsules, granules, tablets, and powders, or in a liquid form, e.g. drink, syrups, and suspension. The composition of the invention may be combined with one or more vectors or excipients, or supplemented with surfactants, lytic agents, stabilizer, emulsifiers, concentrates, sweeteners, or preservatives.

According to another embodiment of the present invention, the composition may be in a form of food. The food composition includes but is not limited to milk, fermented milk, drink, sports beverage, nutrition additive, dietary supplement, candy, or gelatin.

It is found in one example of the present invention, *L. gasseri* PM-A0005 or the composition comprising the strain can increase the PPARγ expression in the lung after administration of the composition to the subject. In particular, the composition can increase the PPARγ expression in the lung draining lymph node of the subject.

It is also found in another example of the invention, *L. gasseri* PM-A0005 or the composition comprising the strain can increase the PPARγ expression in the gut of a subject. In particular, the composition can increase the PPARγ expression in the mesenteric lymph node of the subject.

The present invention is further illustrated by the following examples, which are provided for the purpose of demonstration rather than limitation.

EXAMPLE

1. Materials

BALB/cBYJ mice were obtained from the Laboratory Animal Center of the College of Medicine, National Cheng Kung University. C57BL/6JNarl mice were obtained from National Laboratory Animal Center. Both BALB/cBYJ and C57BL/6JNarl mice, as well as PPARγ P465L mutant mice with half PPARγ expression rate (Tsai, Y. S. et al., *J Clin Invest* (2004) 114, 240-249) were female and age 6 to 8 weeks. All experimental animal care and treatment followed the guidelines set up by the National Institutes of Health Guide for the Care and Use of Laboratory. *Dermatophagoides pteronyssinus* (Der p) extract (1 g lyophilized whole body extract in ether; Allergon, Engelholm, Sweden) was dissolved in pyogenic-free isotonic saline, filtered through a 0.22-mm filter, and stored at 27° C. before use. LPS concentration of the Der p preparations was <0.96 EU/mg of Der p (limulus amebocyte lysate test, E-Toxate; Sigma-Aldrich, St Louis, Mo.).

2. Preparation of the *L. gasseri* PM-A0005

A freeze-dried powder of *L. gasseri* PM-A0005 at concentration of $1.04 \times 10^{11}$ CFU/g was dissolved in pyogenic-free isotonic saline to the concentrations of $5 \times 10^7$ CFU/ml and $5 \times 10^9$ CFU/ml, respectively, and store at −80° C. before use.

3. Administration of *L. gasseri* PM-A0005, Mite Allergen Sensitization and Challenge in Mice Mice were fed daily with 200 μl of normal saline (control group), 200 μl of *L. gasseri* PM-A0005 at $5 \times 10^7$ CFU/ml (low dosage group), or 200 μl of *L. gasseri* PM-A0005 at $5 \times 10^9$ CFU/ml (high dosage group) for two weeks before the experiment until day 13 (except day 0, day 7 and day 14 for mite allergen sensitization), mice were sensitized by subcutaneously injection at tail with a mixture of equal amount of Der p extract at concentration of 1.6 mg/ml and incomplete Freund adjuvant at day 0 and day 7. At day 14, mice were intratracheally challenged with 50 μg Der p extract after anesthetization and subsequently sacrificed at day 17 after airway resistance measurement at day 16.

4. Administration of PPARγ Reagents in Mice

Mite allergen sensitization model in mice was the same as described above, except that the mice were administered with PPARγ agonist or antagonist at day 12 to day 15. Rosiglitazone (PPARγ agonist) was dissolved in DMSO followed by diluted to 5 mg/ml with isotonic saline, then provided to mice in an amount of 5 mg/Kg. On the other hand, GW9662 (PPARγ antagonist) was dissolved in DMSO followed by diluted to 5 mg/ml with isotonic saline, then delivered to the mice by intratracheal injection in an amount of 5 mg/Kg. The mice were sacrificed at day 17 after airway resistance measurement at day 16.

5. Mite Allergen Sensitization and Challenge in C57BL/6JNarl Mice or PPARγ P465L Mutant Mice PPARγ mutation mice or normal mice (C57BL/65Narl) were anesthetized with anesthetic (Zoletil 50 and Rompom in the ratio of 5:1) by intraperitoneal injection, followed by intranasally administered 10 μg of Der p extract daily for 11 days. The mice were sacrificed at day 14 after airway resistance measurement at day 13.

6. Administration of *L. gasseri* PM-A0005 in C57BL/6JNarl Mice or PPARγ P465L Mutant Mice Mite allergen sensitization model in mice was the same as described above, except that the mice were administered daily with $10^9$ CFU of *L. gasseri* PM-A0005 from 2 weeks of the day before mite allergen sensitization. Mice were evaluated with airway resistance measurement at day 13 and sacrificed at day 14.

7. Measurement of Airway Resistance

The airway resistance of mice was measured by a single-chamber, unrestrained whole-body plethysmograph (Buxco Electronics, Inc., Troy, N.Y.) before they were euthanized. Airway resistance was expressed as enhanced pause (Penh). Different dosages of methacholine dissolved in PBS (6.25 mg/ml, 12.5 mg/ml, 25 mg/ml, and 50 mg/ml) were administered by spray for 3 minutes, and Penh values were measured over the period of the subsequent 3 minutes.

8. Microarray Gene Chip and Data Analysis

Total lung draining lymph node and mesenteric lymph nodes RNA extraction and isolation were performed using a Qiagen RNAeasy Mini kit according to manufacturer's instructions (Qiagen, Valencia, Calif.). RNA purity and quality were analyzed by Agilent Bioanalyzer 2100 scan (Agilent, Santa Clara, Calif.). Total RNA were amplified and labeled with Cy3 during in vitro transcription. 2 µg Cy3-labeled cRNA was incubated with fragmentation buffer at 60° C. for 30 minutes to obtain nucleotide fragments average from 50 to 100 and then hybridized with Affymetrix mouse 430 2.0 chips (Affymetrix, Santa Clara, Calif.) at 60° C. for 17 hours. Signal intensities and detection cells were extracted using dChip (v. 2006). Signal intensities of experimental groups were normalized and screened in comparison with positive control group to obtain genes with expression levels over 2 fold change in the low dosage or high dosage group, which were subsequently analyzed with Ingenuity Pathway Analysis database. In addition, common genes with expression levels 2 fold higher than the control group in the low dosage group but lower than control group in the high dosage group were selected for clustering analysis. Clustering analysis was also performed on common genes with expression levels that were 2 fold higher than the control group in the high dosage group but lower than control group in the low dosage group.

Results

Example 1

Physiological Health Conditions of Mice Were Not Affected by Administering Different Dosages of *L. gasseri* PM-A0005

Effects on physiological health conditions of mice after feeding low dosage ($1 \times 10^7$ CFU) or high dosage ($1 \times 10^9$ CFU) of *L. gasseri* PM-A0005 were evaluated. As shown in FIG. 1, body weight of mice slightly decreased one week after feeding and gradually increased until the first mite allergen sensitization. It was also found that in the high dosage group and positive control group, body weight of mice decreased due to the inflammatory response induced by mite allergen sensitization. On the other hand, body weight of mice in the low dosage group was not affected but increased steadily. Loss of hair or death due to infection was not observed during the process of experiment, which demonstrated that the physiological health conditions of mice was not affected by administering different dosages of *L. gasseri* PM-A0005.

Example 2

RNA Microarray Gene Chip Analysis for Mice Administered with Different Dosages of *L. gasseri* PM-A0005

A. Lung Draining Lymph Node Gene Expression

Microarray analysis results showed that in the low dosage group, there were 682 genes with expression levels 2 fold higher than the positive control group. Clustering analysis was performed on these 682 genes with Ingenuity Pathway Analysis (IPA) database and the results demonstrated that these genes involve lipid metabolism and molecular transport pathway. In the high dosage group, there were 643 genes with expression levels 2 fold higher than positive control group, and clustering analysis demonstrated that these genes involve tissue morphology and development and function of skeletal and muscle system. 349 genes were identified in both the low dosage and high dosage group. In the low dosage group, 202 genes were identified as expression levels 2 fold lower than positive control group, and 249 genes were identified in the high dosage group, wherein 148 genes existed in both groups. Those analysis results demonstrated that gene expression patterns between low dosage group and high dosage group have no significant difference.

B. Mesenteric Lymph Node Gene Expression

Microarray analysis results showed that in the low dosage group, there were 765 genes with expression levels 2 fold higher than the positive control group. IPA results were similar with those of lung draining lymph node gene expression and demonstrated that these genes involve mainly lipid metabolism and molecular transport pathway. In the high dosage group, there were 391 genes with expression levels 2 fold higher than positive control group, and clustering analysis demonstrated that these genes involve apoptosis and cell cycle. 58 genes were existed in both the low dosage and high dosage group. In the low dosage group, 1275 genes were identified with expression levels 2 fold lower than the positive control group, and 449 genes were identified in the high dosage group, wherein 52 genes existed in both groups.

Example 3

Figure 2:
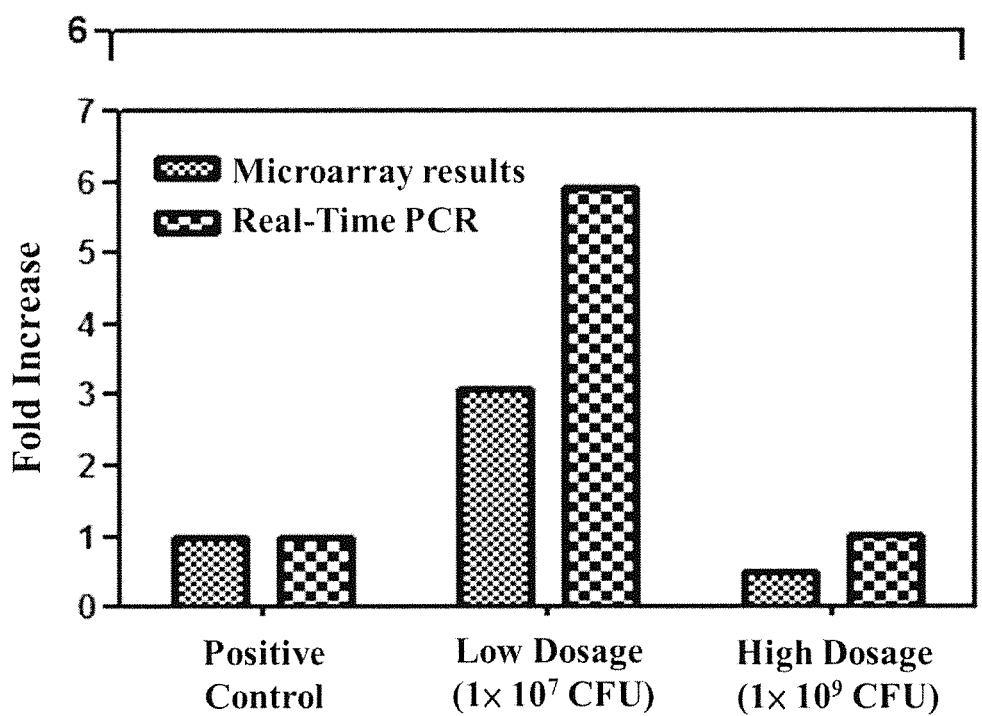
FIG. 2 shows the microarray gene chip and Real-Time PCR analysis results for PPARγ expression in the lung draining lymph node and mesenteric lymph node of mice fed with different dosage of L. gasseri PM-A0005: (a) PPARγ expression in the lung draining lymph node; and (b) PPARγ expression in the mesenteric lymph node.

Administration of *L. gasseri* PM-A0005 Affects Mice PPARγ Gene Expression In Vivo Microarray analysis results demonstrated that the administration of *L. gasseri* PM-A0005 induced expression level variation in lipid metabolism related genes, for example, PPARγ. Real-Time PCR was conducted to confirm the gene expression pattern was identical to the microarray analysis results. As shown in FIG. 2(*a*), in lung draining lymph node, both the low dosage and high dosage of *L. gasseri* PM-A0005 induced PPARγ expression higher than the positive control group. On the other hand, in the mesenteric lymph node, a low dosage of *L. gasseri* PM-A0005 induced PPARγ expression, but a high dosage of *L. gasseri* PM-A0005 inhibits PPARγ expression.

Figure 3:
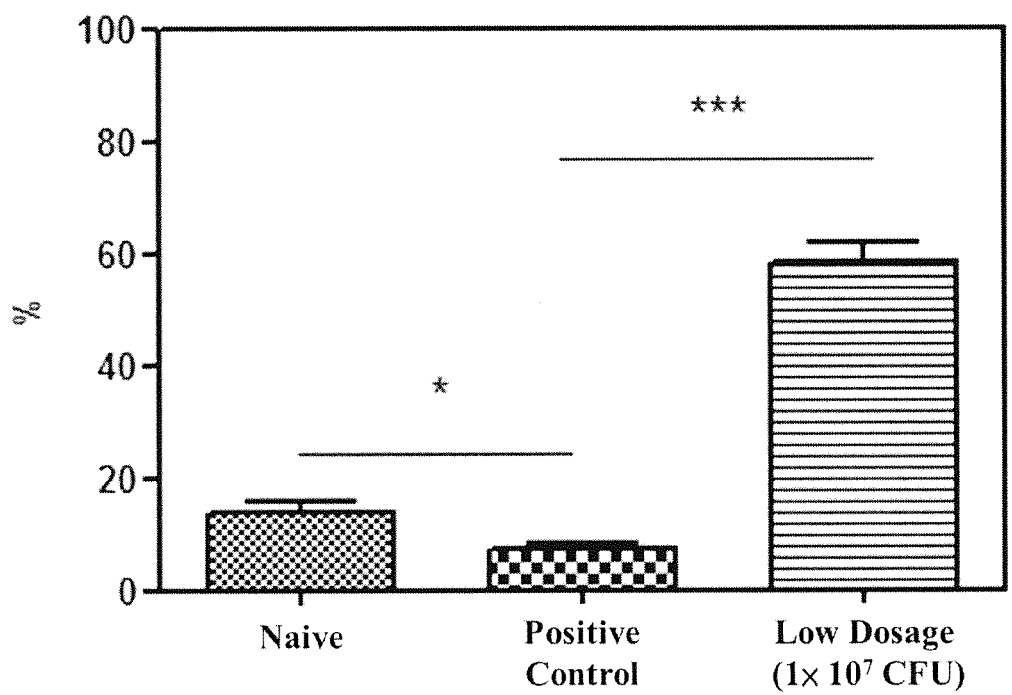
FIG. 3 shows quantitative results of PPARγ immunohistochemistry staining for the lung section of mice.

To evaluate if the administration of *L. gasseri* PM-A0005 in allergic asthma mice could promote lung PPARγ expression, lung sections from naive group, positive control group and low dosage group ($1 \times 10^7$ CFU) were stained with immunohistochemistry staining, and PPARγ expression levels were quantified. Analysis results revealed that PPARγ expression level in lung tissue of mite allergen sensitized mice was significant lower than that in normal control group, but administration of $1 \times 10^7$ CFU *L. gasseri* PM-A0005 daily could increase PPARγ expression level, which was significant higher than that in normal control group (FIG. 3).

Example 4

Figure 4:
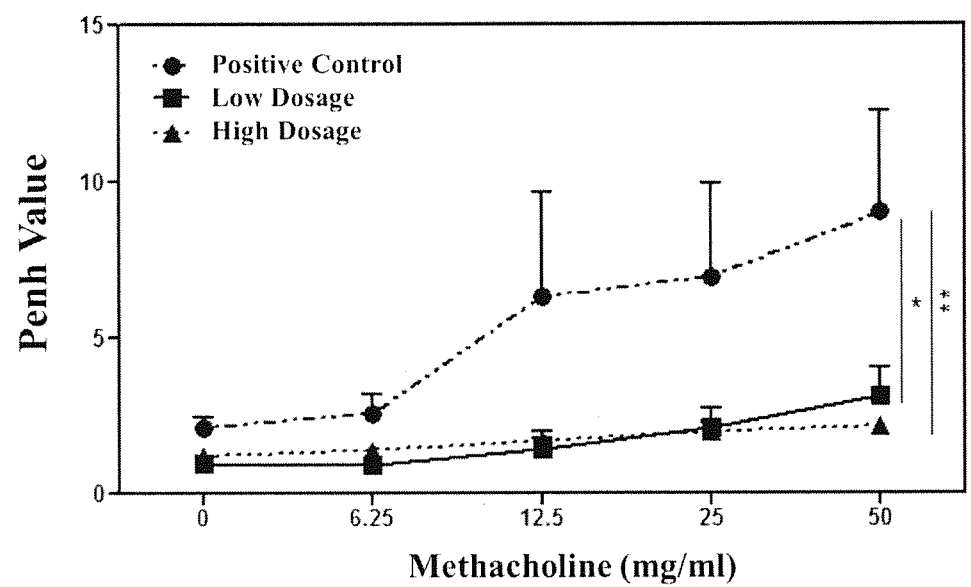
FIG. 4 shows airway resistance of mice administered with different dosage of L. gasseri PM-A0005 (wherein Penh value was used for evaluating airway resistance from different treatment groups of mice through elevated concentrations of methacholine).

Administration of Different Dosages of *L. gasseri* PM-A0005 Reduces Mice Airway Hyperresponsiveness A single-chamber, unrestrained whole-body plethysmograph was used for measuring airway resistance of mice, expressed as enhanced pause (Penh) value. Higher Penh value refers to higher airway resistance, i.e. hyperresponsiveness. The analysis results showed that in the positive control group (mice sensitized with mite allergen), Penh value increased with the elevation of methacholine concentration, but administration of different dosages of *L. gasseri* PM-A0005 could significantly reduce mice airway hyperresponsiveness (FIG. 4).

Example 5

Figure 5:
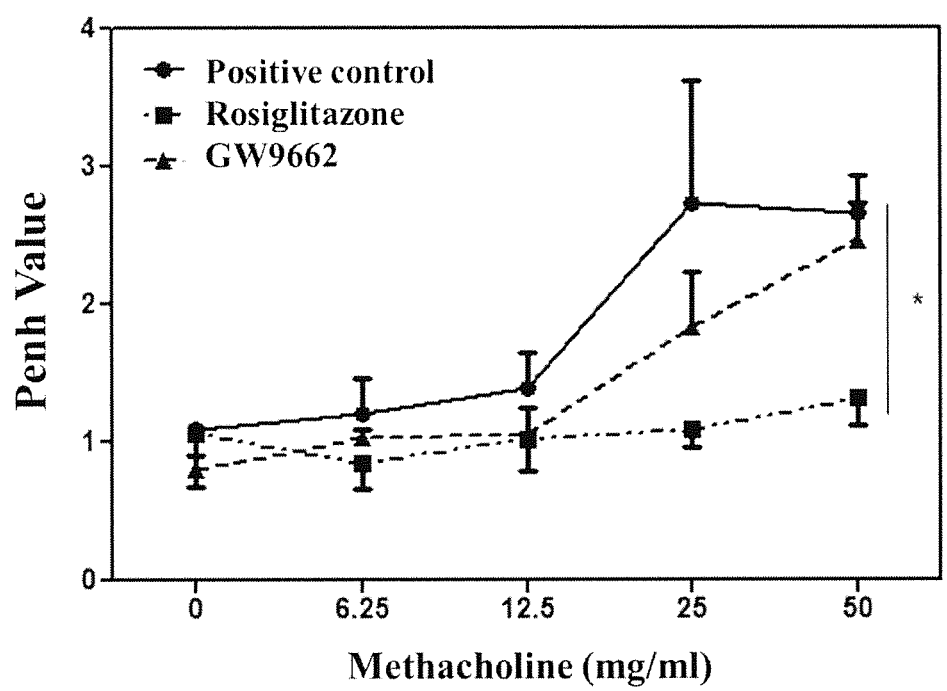
FIG. 5 shows airway resistance of mice administered with PPARγ agonist Rosiglitazone and PPARγ antagonist GW9662 (wherein Penh value was used for evaluating airway resistance from different treatment groups of mice through elevated concentrations of methacholine).
Figure 6:
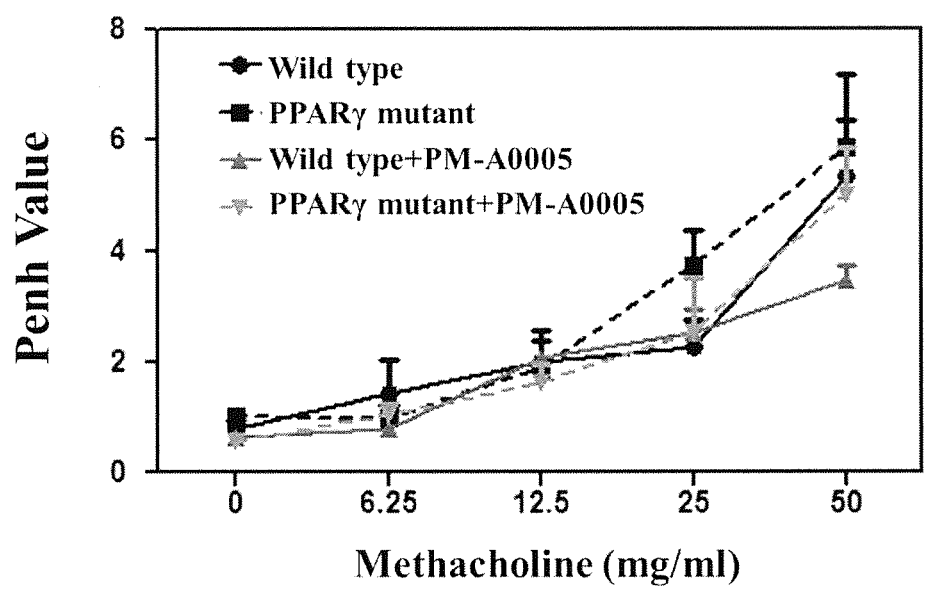
FIG. 6 shows airway resistance of PPARγ P465L mutant mice and wild type mice administered with L. gasseri PM-A0005 (wherein Penh value was used for evaluating airway resistance from different treatment groups of mice through elevated concentrations of methacholine).

Administration of PPARγ Agonist Effectively Reduces Mice Airway Hyperresponsiveness As shown in FIG. 5, in the positive control group (mice sensitized with mite allergen) and GW9662 treatment group, Penh value increased with the elevation of methacholine concentration, but administration of Rosiglitazone could significantly reduce mice airway hyperresponsiveness. The analysis results demonstrated that administration of Rosiglitazone could improve lung function.

Comparison Example 1

Airway Hyperresponsiveness could not be Reduced by Administration of *L. gasseri* PM-A0005 in PPARγ P465L Mutant Mice The experimental results revealed that administration of *L. gasseri* PM-A0005 could reduce airway hyperresponsiveness in wild type mice, but not in the PPARγ P465L mutation mice. Penh value increased with the elevation of methacholine concentration, demonstrating that *L. gasseri* PM-A0005 could not reduce airway hyperresponsiveness in PPARγ P465L mutation mice.

It will be understood by those skilled in the art that changes could be made to the embodiments described above without departing from the broad inventive concept thereof. It is therefore understood that this invention is not limited to the particular embodiments disclosed, but it is intended to cover modifications within the spirit and scope of the present invention as defined by the appended claims.

We claim:

1. A method for enhancing peroxisome proliferator-activated receptor γ (PPARγ) expression in a subject in need thereof, comprising administering to the subject in need thereof an effective amount of *Lactobacillus gasseri* PM-A0005, which was deposited in the China Center for Type Culture Collection (CCTCC), China, with Deposit No. M 207039.

2. The method of claim 1, wherein the *Lactobacillus gasseri* PM-A0005 is orally administered to the subject.

3. The method of claim 2, wherein the effective amount of the *Lactobacillus gasseri* PM-A0005 is between $1 \times 10^8$ CFU/kg/day to $1 \times 10^9$ CFU/kg/day of the body weight of the subject.

4. The method of claim 3, wherein the effective amount of the *Lactobacillus gasseri* PM-A0005 is between $5 \times 10^8$ CFU/kg/day to $6 \times 10^8$ CFU/kg/day of the body weight of the subject.

5. The method of claim 4, wherein the effective amount of the *Lactobacillus gasseri* PM-A005 is about $55 \times 10^8$ CFU/kg/day of the body weight of the subject.

6. The method of claim 1, wherein the he *Lactobacillus gasseri* PM-A0005 is in a form of a composition.

7. The method of claim 6, wherein the composition is a pharmaceutical composition.

8. The method of claim 6, wherein the composition is a food composition.

9. The method of claim 8, wherein the food composition is milk, fermented milk, a drink, a sports beverage, a nutritional additive, a dietary supplement, candy, or gelatin.

10. The method of claim 1, wherein the PPARγ expression increases in the lung of the subject.

11. The method of claim 1, wherein the PPARγ expression increases in the lung draining lymph node of the subject.

12. The method of claim 1, wherein the PPARγ expression increases in the gut of the subject.

13. The method of claim 12, wherein the PPARγ expression increases in the mesenteric lymph node of the subject.

* * * * *